United States Patent
Ding et al.

(10) Patent No.: US 9,120,719 B2
(45) Date of Patent: Sep. 1, 2015

(54) PHOSPHIDE CATALYST FOR SYNGAS CONVERSION AND THE PRODUCTION METHOD AND USE THEREOF

(75) Inventors: Yunjie Ding, Dalian (CN); Xiangen Song, Dalian (CN); Weimiao Chen, Dalian (CN); Li Yan, Dalian (CN); Yuan Lv, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 15 days.

(21) Appl. No.: 13/988,565

(22) PCT Filed: Jul. 12, 2012

(86) PCT No.: PCT/CN2012/078544
§ 371 (c)(1),
(2), (4) Date: May 21, 2013

(87) PCT Pub. No.: WO2014/005347
PCT Pub. Date: Jan. 9, 2014

(65) Prior Publication Data
US 2014/0018455 A1  Jan. 16, 2014

(30) Foreign Application Priority Data

Jul. 5, 2012  (CN) .......................... 2012 1 0231677

(51) Int. Cl.
| | | |
|---|---|---|
| *B01J 27/00* | (2006.01) | |
| *B01J 27/185* | (2006.01) | |
| *B01J 27/182* | (2006.01) | |
| *B01J 21/00* | (2006.01) | |
| *B01J 37/18* | (2006.01) | |
| *C07C 9/04* | (2006.01) | |
| *C07C 9/06* | (2006.01) | |
| *C07C 27/00* | (2006.01) | |
| *C07C 27/06* | (2006.01) | |
| *C07C 31/04* | (2006.01) | |
| *C07C 31/08* | (2006.01) | |
| *C07C 27/22* | (2006.01) | |
| *C07C 1/04* | (2006.01) | |
| *C07C 29/156* | (2006.01) | |
| *B01J 37/03* | (2006.01) | |
| *B01J 23/74* | (2006.01) | |
| *B01J 35/02* | (2006.01) | |
| *B01J 35/10* | (2006.01) | |
| *B01J 37/02* | (2006.01) | |
| *C10G 2/00* | (2006.01) | |

(52) U.S. Cl.
CPC ................ *C07C 27/22* (2013.01); *B01J 23/74* (2013.01); *B01J 27/1853* (2013.01); *B01J 35/023* (2013.01); *B01J 35/1019* (2013.01); *B01J 35/1023* (2013.01); *B01J 35/1061* (2013.01); *B01J 35/1066* (2013.01); *B01J 37/0201* (2013.01); *B01J 37/031* (2013.01); *C07C 1/044* (2013.01); *C07C 1/0425* (2013.01); *C07C 1/0435* (2013.01); *C07C 29/156* (2013.01); *C10G 2/332* (2013.01); *C10G 2/341* (2013.01); *C10G 2/342* (2013.01); *B01J 37/18* (2013.01); *C07C 2521/04* (2013.01); *C07C 2521/08* (2013.01); *C07C 2523/745* (2013.01); *C07C 2523/75* (2013.01); *C07C 2523/755* (2013.01); *C07C 2527/185* (2013.01)

(58) Field of Classification Search
CPC .. B01J 27/1853; B01J 37/0201; B01J 37/031; B01J 37/088; B01J 37/18; C07C 9/04; C07C 9/06; C07C 27/00; C07C 27/06; C07C 31/04; C07C 31/08
USPC .......... 502/208, 213, 214, 258–260; 518/715, 518/719, 721
See application file for complete search history.

(56) References Cited

U.S. PATENT DOCUMENTS

| | | | | |
|---|---|---|---|---|
| 4,454,246 | A * | 6/1984 | Fung ............................. | 502/213 |
| 7,446,075 | B1 * | 11/2008 | Kolev .......................... | 502/208 |
| 2008/0099375 | A1 * | 5/2008 | Landau et al. ................. | 208/244 |

FOREIGN PATENT DOCUMENTS

| | | | | |
|---|---|---|---|---|
| CN | 1516685 A | | 7/2004 | |
| CN | 1764501 A | | 4/2006 | |
| CN | 101168132 A | | 4/2008 | |
| WO | 01/23501 | * | 4/2001 | ............. C10G 45/04 |
| WO | 2011049456 A1 | | 4/2011 | |
| WO | 2014/005347 | * | 1/2014 | ............. B01J 27/185 |

OTHER PUBLICATIONS

Zaman et al., Catalysis Today 171 (2011) 266— 274.
Zaman et al., Applied Catalysis a: General 378 (2010) 59-68.
Chen et al., "Study on the Technology of Synthesis Dimethyl Ether with Bi-function Catalyst by Phosphorus Modified", Journal of Wuhan University of Technology, vol. 33, No. 8, Aug. 2011, pp. 118-122.
International Search Report and Written Opinion dated Apr. 18, 2013 for PCT/CN2012/078544.

* cited by examiner

*Primary Examiner* — Patricia L Hailey
(74) *Attorney, Agent, or Firm* — Enshan Hong; VLP Law Group LLP

(57) ABSTRACT

This invention provides a phosphide catalyst for syngas conversion and the production method and use thereof, more specifically, to a catalyst for converting a syngas raw material into oxygenates, comprising one or more metallic Fe, Co, Ni and their phosphides, the production method of the catalyst and its use in the reaction of converting a syngas raw material into hydrocarbons and oxygenates. According to the invention, a catalyst for converting $H_2/CO$ into hydrocarbons and oxygenates, supported by $SiO_2$ or $Al_2O_3$ and comprising one or more metallic Fe, Co, Ni and their phosphides under certain reaction temperatures and pressures is provided. The catalysts are consisted of two parts of an active component and a support. The active component is a mixture consisted of one or more of metallic Fe, Co, Ni and their phosphides. The support is selected from $SiO_2$ or $Al_2O_3$. In a fix-bed or slurry bed reactor, $H_2/CO$ can be converted into oxygenates having two carbons or more and hydrocarbons with high activity and high selectivity, under certain reaction temperatures and pressures and the action of the catalyst in the invention.

10 Claims, No Drawings

PHOSPHIDE CATALYST FOR SYNGAS CONVERSION AND THE PRODUCTION METHOD AND USE THEREOF

PRIORITY CLAIM

This is a U.S. national stage of application No. PCT/CN2012/078544, filed on Jul. 12, 2012. Priority is claimed on the following application: Country: China, Application No.: 201210231677.7, Filed: Jul. 5, 2012, the content of which is/are incorporated here by reference.

FIELD OF THE INVENTION

This invention relates to a catalyst for converting a syngas raw material into hydrocarbons and oxygenates, supported by $SiO_2$ or $Al_2O_3$ and comprising a mixture consisted of one or more metallic Fe, Co, Ni and their phosphides, and the production method and use thereof, more specifically, to a catalyst for producing efficiently oxygenates having two carbons or more by using a mixed gas of CO and $H_2$ under a certain temperature and pressure, supported by $SiO_2$ or $Al_2O_3$ and comprising a mixture consisted of one or more metallic Fe, Co, Ni and their phosphides, and the production method and use thereof.

BACKGROUND OF THE INVENTION

The development of "green fuel" by using technologies for cleaning efficiently coal resources has important strategy meaning and use foreground from the point of resource utilization and environmental protection as China being largest coal-output country in the world.

The synthesis of hydrocarbons and oxygenates by catalytic hydrogenation of CO is one of the important approaches for clean utilization of coal resource. In recent year, the use value of lower carbon mixed alcohols in the field of fuel and chemical industry appears stepwise, and the related researches are active increasingly.

Homogeneous catalysts for synthesis of lower carbon mixed alcohols can be broadly grouped into two categories of noble metal and non noble metal, wherein noble metal Rh catalyst can convert syngas into ethanol and other oxygenates having two carbons or more. However, Rh metal is expensive due to the limited supply, thus the scale in commercial use thereof is limited. On the other hand, the main non noble metal catalysts for producing lower carbon mixed alcohols from syngas comprises modified methanol synthesis catalysts, modified Fischer-Tropsch (F-T) synthesis catalysts; and alkali metal-doped Mo catalysts. Among these catalysts, representative catalyst systems having industrial use foreground can be grouped into the following 4 categories:

(1) MoS catalyst system developed by Dow Chemical Company (Sygmol process);

(2) Cu—Co catalyst system developed by French Institute of Petroleum Institute (IFP process);

(3) Cu—Zn—Al catalyst system developed by Lurgi Company (Octamix process); and (4) Zn—Cr—K catalyst system developed by Sham Company (MAS process).

In spite of the individual outstanding features of the above 4 catalyst systems, the developed catalysts have insufficiency in terms of activity, selectivity, stability, economy, and the like. The development of catalysts having high activity and high selectivity toward oxygenates having two carbons or more is still the difficulty and key point of the researches. Although the researchers had made a great deal of efforts on the development of these catalyst systems, there is still a very large space to improve the catalytic activity and selectivity toward higher alcohols.

Transition metal phosphides, being an important hydrogenation catalyst, show similar properties of noble metals in many reactions involving hydrogen and have the potential possibility for replacing noble metal catalysts. Kevin J. Smith et. al. (*Appl. Catal., A* 2010, 378, 59-68, *Catal. Today* 2011, 171, 266-274) studied the use of molybdenum phosphide catalyst in the hydrogenation reaction of CO, showing that the products thereof are significantly different with those in the case where conventional non-noble metal catalysts are used. The content of oxygenated products having two carbons or more in the liquid phase products reaches to 76% (C %).

SUMMARY OF THE INVENTION

One object of this invention is to provide a catalyst for converting a syngas raw material into hydrocarbons and oxygenates, supported by $SiO_2$ or $Al_2O_3$ and comprising a mixture consisted of one or more metallic Fe, Co, Ni and their phosphides, the production method of the catalyst and its use in the reaction of converting a syngas raw material into hydrocarbons and oxygenates. Compared with prior art, the catalyst of the invention does not employ noble metal such as Rh and the like, and at the same time, achieves higher activity and selectivity towards oxygenates having two carbons or more.

In order to achieve the above object, the invention, in one aspect, provides a supported catalyst for converting a syngas raw material into hydrocarbons and oxygenates, wherein the supported catalyst includes an active component and a support; the active component is a mixture consisting of a transition metal and a phosphide of the transition metal, wherein the transition metal is one or more of Fe, Co, and Ni, wherein the weight percent of the active component in terms of metal is 0.5 to 30.0% by weight of the catalyst, wherein in the active component, the ratio of the mole number of the transition metal to the mole number of the phosphorous atoms is in the range of 1 to 10; and the supports are $SiO_2$ or $Al_2O_3$; wherein the $SiO_2$ has a specific surface area of 100 to 600 m$^2$/g, and an average pore size of 5 to 90 nm; and the $Al_2O_3$ has a specific surface area of 100 to 400 m$^2$/g, and an average pore size of 4 to 90 nm.

In a preferable embodiment of the invention, the weight percent of the active component in terms of metal is 1.0 to 25.0% by weight of the catalyst.

In another preferable embodiment of the invention, the $SiO_2$ has a specific surface area of 200 to 400 m$^2$/g, and an average pore size of 10 to 50 nm.

In another preferable embodiment of the invention, the $Al_2O_3$ has a specific surface area of 150 to 300 m$^2$/g, and an average pore size of 10 to 50 nm.

In another particularly preferable embodiment of the invention, the supported catalyst is consisted of the active component and the support.

The invention, in another aspect, provides a method for producing hydrocarbons and oxygenates, comprising converting a syngas raw material into hydrocarbons and oxygenates, in the presence of the above-mentioned catalyst, in a reactor.

In a preferable embodiment of the invention, the reactor is a fixed bed or slurry bed reactor.

In another preferable embodiment of the invention, the method is performed under conditions of a temperature being 100 to 400° C., a reaction pressure being 1.0 to 10.0 MPa gauge, a CO/$H_2$ ratio by mole in the syngas being 0.5/1 to 10/1 and a space velocity being 100 to 10000 h$^{-1}$.

The invention, in a further aspect, provides a method for producing the above mentioned catalyst, comprising supporting the active component on the support via an impregnation process or a precipitation process, and then calcining the resultant in air at high temperature.

In a preferable embodiment of the invention, the method further comprises temperature-program reducing the calcined catalyst in $H_2$ flow.

DETAILED DESCRIPTION OF THE PREFERRED EMBODIMENT

In the following, the disclosure of the invention is described in detail. This invention provides a catalyst for converting a syngas raw material into hydrocarbons and oxygenates, consisting of two parts of an active component and a support, therein the weight percent of the active component is 0.5 to 30.0%. The active component is a mixture consisting of a transition metal and a phosphide of the transition metal, wherein the transition metal is one or more of Fe, Co, and Ni, wherein the weight percent of the active component in terms of metal is 0.5 to 30.0% by weight of the catalyst, wherein in the active component, the ratio of the mole number of the transition metal to the mole number of the phosphorous atoms is in the range of 1 to 10; and the supports are $SiO_2$ or $Al_2O_3$; wherein the $SiO_2$ has a specific surface area of 100 to 600 $m^2/g$, and an average pore size of 5 to 90 nm; and the $Al_2O_3$ has a specific surface area of 100 to 400 $m^2/g$, and an average pore size of 4 to 90 nm.

The phosphides of the transition metal Fe, Ni, and Co possess similar catalytic properties of noble metals, and show similar properties of metals during the CO adsorption and hydrogenation reaction. In general, metallic Fe, Ni, and Co catalyst has catalytic properties of producing hydrocarbons while rarely generating oxygenates, via a CO hydrogenation. Moreover, the metallic catalyst has a feature of extending carbon chain in the CO hydrogenation reaction. Further, the above phosphides of the transition metal Fe, Ni, and Co often have the property of adsorbing and activating CO. Thus, it can be expected that this kind of catalyst will have the possibility of hydrogenating CO to produce oxygenates having two carbons or more. The use of the oxide support with high specific surface area can improve the dispersion of the metal supported, so as to increase the utilization ratio of the transition metal Fe, Ni, and Co. Meanwhile, the high dispersed metal often favors the formation of phosphides. $SiO_2$ and $Al_2O_3$ are supports often used for producing supported catalyst.

The catalyst of this vention is used for the reaction of efficiently producing oxygenates having two carbons or more by using a mixed gas of CO and $H_2$ as raw material, under certain reaction temperatures and pressures. The catalyst is consisted of the two parts of the active component and the support. The active component is a mixture consisting of one or more of metallic Fe, Co and Ni and their phosphides. The support is selected from $SiO_2$ or $Al_2O_3$ or the like. In a fix-bed or slurry bed reactor, CO is performed a hydrogenation reaction by using CO/$H_2$ as reaction raw material under the action of the catalyst which can be converted into oxygenates having two carbons or more with high activity and high selectivity.

Oxygenates may include methanol and other oxygenates having two carbons or more. The examples of oxygenates having two carbons or more may include: ethanol and acetaldehyde, propanol and propylaldehyde, butanol and butyraldehyde, and the like.

Hydrocarbons may include alkanes such as methane, ethane, propane, and butane; and olefins such as ethane, propene, and butene; and the like.

The main products produced from the reaction for efficiently producing oxygenates having two carbons or more by using a mixed gas of CO and $H_2$ as raw material in the presence of the catalyst of the invention may include ethanol, acetaldehyde, propanol, propylaldehyde, butanol and pentanol and the like.

The lower carbon as described herein means five carbons or less. For example, lower carbon mixed alcohols means mixed alcohols having five carbons or less.

"The mixture consisting of one or more of metallic Fe, Co and Ni and their phosphides" means that the mixture can be consisted of any one of metallic Fe, Co and Ni and the phosphide thereof, or can be consisted of any two of metallic Fe, Co and Ni and the phosphides thereof, or can be consisted of the three of metallic Fe, Co and Ni and the phosphides thereof.

In the case there the mixture is consisted of any one of metallic Fe, Co and Ni and the phosphide thereof, the examples of the mixture may include a mixture consisted of Fe and the phosphide thereof, Co and the phosphide thereof, and Ni and the phosphide thereof.

In the case there the mixture is consisted of any two of metallic Fe, Co and Ni and the phosphide thereof, the examples of the mixture may include a mixture consisted of Fe and Co and the phosphides thereof, Fe and Ni and the phosphides thereof, and Co and Ni and the phosphides thereof.

In the reaction system of the invention, Co/$H_2$ may be directly passed into in a fix-bed or slurry bed reactor filled with the granular or powered catalyst of the invention to perform the CO hydrogenation reaction.

In the catalyst of the invention, the preferable weight percent content of the transition metal is 0.5 to 30.0%, the most preferable content by weight is 1.0 to 25.0%. The support may be selected from $SiO_2$ which has preferably a specific surface area of 100 to 600 $m^2/g$, and preferably an average pore size of 5 to 90 nm, and most preferably a specific surface area of 200 to 400 $m^2/g$, and most preferably an average pore size of 10 to 50 nm. The support may also be selected from $Al_2O_3$, wherein $Al_2O_3$ has preferably a specific surface area of 100 to 400 $m^2/g$, and preferably an average pore size of 4 to 90 nm, and most preferably a specific surface area of 150 to 300 $m^2/g$, and most preferably an average pore size of 10 to 50 nm.

A method for producing the catalyst of the invention may comprise the steps of: using $SiO_2$ or $Al_2O_3$ as the support, using metal nitrates and ammonium hydrogen phosphate as metal and phosphorous sources to formulate an aqueous solution, impregnating them on the support via impregnation method or depositing them on the surface of the support via deposition method, drying or thermal drying, baking the resultant at high temperature to obtain an oxidation state precursor. After being temperature-programm reduced in $H_2$ flow, the catalyst comprising a mixture consisted of one or more of metallic Fe, Co and Ni and their phosphides is obtained.

In the invention, after the oxidation state precursor being temperature-programm reduced in $H_2$ flow, in the catalyst comprising a mixture consisted of one or more of metallic Fe, Co and Ni and their phosphides, the ratio of the amount by mole of the metal to the amount by mole of the phosphides in terms of phosphorous is in the range of 1 to 10.

In the phosphides of any one of the metal atoms Fe, Co, and Ni, the metal atoms form the minimum structural units of a triangular prism structure, while these triangular prism units forms in different bonding manner into different kinds of crystal lattices; while P atoms occupy the void interior the triangular prism. Due to the insertion of P atoms, the bulk property of the parent metal takes place a change. This is mainly caused by the interaction of the ligand effect and electronic effect. On one aspect, the electrons may transfer between the metal and the ligand, and on the other aspect, the number of metal atoms exposed on the surface is decreased due to the insertion of the ligand, such that both the electron configuration and the lattice configuration of this kind of compounds are changed significantly, as compared with the parent metal. In these crystals with different crystallographic forms, being influenced by P, both the electronic structure and the adsorption property of the metal are changed significantly, causing the difference of the catalytic performance.

Before use, the oxidation state precursor of each catalyst is reduced and activated in-situ in $H_2$ (GHSV=1000 to 10000 $h^{-1}$) flow in a fix-bed reactor, under conditions of atmospheric pressure, and a temperature increasing from room temperature to 300 to 400° C. at 1 to 10° C./min and from 300 to 400° C. to 500 to 700° C. at 0.5 to 3° C./min, holding 1 to 6 h and then decreasing in $H_2$ flow to the reaction temperature, to obtain the catalyst.

In the reaction for efficiently producing oxygenates having two carbons or more by using a mixed gas of CO and $H_2$ as raw material, the reaction temperature is about 280° C., the reaction pressure is about 5.0 MPa, CO/$H_2$=about 2/1(molar ratio), and the space velocity is about 5000 $h^{-1}$.

The invention is further illustrated by the specific examples in the following. Unless indicated specifically, ratios, parts, and percentages described in the application are all based on weight.

The materials used in the examples are as follows:

Ferric nitrate ($Fe(NO_3)_3.9H_2O$), purchased from Tianjin Kermel Chemical Reagent Development Center, analytical pure Cobalt nitrate ($Co(NO_3)_2.6H_2O$), purchased from Tianjin Kermel Chemical Reagent Development Center, analytical pure Nickel nitrate ($Ni(NO_3)_2.6H_2O$), purchased from Tianjin Kermel Chemical Reagent Development Center, analytical pure Diammonium hydrogen phosphate (($NH_4$)$HPO_4$), purchased from Shenyang Union Reagent Plant, analytical pure Silica (($SiO_2$)), purchased from Qingdao Ocean Chemical Plant, $d_{particle}$=0.50 mm, spherical particles, $S_{BET}$=350 $m^2$/g, $d_{pore}$=15.1 nm Alumina ($Al_2O_3$), purchased from the Zibo Bell Chemical Technology Co., Ltd., Shandong, $d_{particle}$=0.50 mm, spherical particles, $S_{BET}$=150 $m^2$/g, $d_{pore}$=12.1 nm X-ray diffraction fluorescence spectroscopy (XRF) is used to determine half-quantitatively the components of the catalysts produced in the Examples.

Example 1

The catalyst in Example 1 was $FeP/SiO_2$ (Fe/P=8, molar ratio). 10.0 g $SiO_2$ (20 to 40 mesh) was weighted. An 8 ml aqueous solution containing 7.21 g $Fe(NO_3)_3.9H_2O$ and 0.29 g ($NH_4$)$_2HPO_4$ was formulated. About 2 ml concentrated $HNO_3$ was added dropwise thereto, and was dissolved by heating. The above $SiO_2$ support was impregnated with the aqueous solution, dried in a water bath at 60° C., and then further dried in the oven at 120° C. for 8 h, and calcined at 450° C. for 4 h. Thus, an oxidation state precursor of the catalyst was obtained.

Example 2

The catalyst in Example 2 was $FeP/SiO_2$ (Fe/P=4, molar ratio). 10.0 g $SiO_2$ (20 to 40 mesh) was weighted. An 8 ml aqueous solution containing 7.21 g $Fe(NO_3)_3.9H_2O$ and 0.58 g ($NH_4$)$_2HPO_4$ was formulated. About 2 ml concentrated $HNO_3$ was added dropwise thereto, and was dissolved by heating. The above $SiO_2$ support was impregnated with the aqueous solution, dried in a water bath at 60° C., and then further dried in the oven at 120° C. for 8 h, and calcined at 450° C. for 4 h. Thus, an oxidation state precursor of the catalyst was obtained.

Example 3

The catalyst in Example 3 was $FeP/SiO_2$ (Fe/P=2, molar ratio). 10.0 g $SiO_2$ (20 to 40 mesh) was weighted. An 8 ml aqueous solution containing 7.21 g $Fe(NO_3)_3.9H_2O$ and 1.17 g ($NH_4$)$_2HPO_4$ was formulated. About 2 ml concentrated $HNO_3$ was added dropwise thereto, and was dissolved by heating. The above $SiO_2$ support was impregnated with the aqueous solution, dried in a water bath at 60° C., and then further dried in the oven at 120° C. for 8 h, and calcined at 450° C. for 4 h. Thus, an oxidation state precursor of the catalyst was obtained.

Example 4

The catalyst in Example 4 was $CoP/SiO_2$(Co/P=8, molar ratio). 10.0 g $SiO_2$ (20 to 40 mesh) was weighted. An 8 ml aqueous solution containing 4.93 g $Co(NO_3)_2.6H_2O$ and 0.29 g ($NH_4$)$_2HPO_4$ was formulated. About 2 ml concentrated $HNO_3$ was added dropwise thereto, and was dissolved by heating. The above $SiO_2$ support was impregnated with the aqueous solution, dried in a water bath at 60° C., and then further dried in the oven at 120° C. for 8 h, and calcined at 450° C. for 4 h. Thus, an oxidation state precursor of the catalyst was obtained.

Example 5

The catalyst in Example 5 was $CoP/SiO_2$ (Co/P=4, molar ratio). 10.0 g $SiO_2$ (20 to 40 mesh) was weighted. An 8 ml aqueous solution containing 4.93 g $Co(NO_3)_2.6H_2O$ and 0.58 g ($NH_4$)$_2HPO_4$ was formulated. About 2 ml concentrated $HNO_3$ was added dropwise thereto, and was dissolved by heating. The above $SiO_2$ support was impregnated with the aqueous solution, dried in a water bath at 60° C., and then further dried in the oven at 120° C. for 8 h, and calcined at 450° C. for 4 h. Thus, an oxidation state precursor of the catalyst was obtained.

Example 6

The catalyst in Example 6 was $CoP/SiO_2$ (Co/P=2, molar ratio). 10.0 g $SiO_2$ (20 to 40 mesh) was weighted. An 8 ml aqueous solution containing 4.93 g $Co(NO_3)_2.6H_2O$ and 1.17 g ($NH_4$)$_2HPO_4$ was formulated. About 2 ml concentrated $HNO_3$ was added dropwise thereto, and was dissolved by heating. The above $SiO_2$ support was impregnated with the aqueous solution, dried in a water bath at 60° C., and then further dried in the oven at 120° C. for 8 h, and calcined at 450° C. for 4 h. Thus, an oxidation state precursor of the catalyst was obtained.

Example 7

The catalyst in Example 7 was $NiP/SiO_2$ (Ni/P=8, molar ratio). 10.0 g $SiO_2$ (20 to 40 mesh) was weighted. An 8 ml aqueous solution containing 4.93 g $Ni(NO_3)_2.6H_2O$ and 0.29 g ($NH_4$)$_2HPO_4$ was formulated. About 2 ml concentrated $HNO_3$ was added dropwise thereto, and was dissolved by heating. The above $SiO_2$ support was impregnated with the aqueous solution, dried in a water bath at 60° C., and then further dried in the oven at 120° C. for 8 h, and calcined at 450° C. for 4 h. Thus, an oxidation state precursor of the catalyst was obtained.

Example 8

The catalyst in Example 8 was NiP/SiO$_2$(Ni/P=4, molar ratio). 10.0 g SiO$_2$ (20 to 40 mesh) was weighted. An 8 ml aqueous solution containing 4.93 g Ni(NO$_3$)$_2$·6H$_2$O and 0.58 g (NH$_4$)$_2$HPO$_4$ was formulated. About 2 ml concentrated HNO$_3$ was added dropwise thereto, and was dissolved by heating. The above SiO$_2$ support was impregnated with the aqueous solution, dried in a water bath at 60° C., and then further dried in the oven at 120° C. for 8 h, and calcined at 450° C. for 4 h. Thus, an oxidation state precursor of the catalyst was obtained.

Example 9

The catalyst in Example 9 was NiP/SiO$_2$(Ni/P=2, molar ratio). 10.0 g SiO$_2$ (20 to 40 mesh) was weighted. An 8 ml aqueous solution containing 4.93 g Ni(NO$_3$)$_2$·6H$_2$O and 1.17 g (NH$_4$)$_2$HPO$_4$ was formulated. About 2 ml concentrated HNO$_3$ was added dropwise thereto, and was dissolved by heating. The above SiO$_2$ support was impregnated with the aqueous solution, dried in a water bath at 60° C., and then further dried in the oven at 120° C. for 8 h, and calcined at 450° C. for 4 h. Thus, an oxidation state precursor of the catalyst was obtained.

Example 10

The catalyst in Example 10 was CoP/Al$_2$O$_3$ (Co/P=4, molar ratio). 10.0 g Al$_2$O$_3$ (20 to 40 mesh) was weighted. An 8 ml aqueous solution containing 4.93 g Co(NO$_3$)$_2$·6H$_2$O and 0.58 g (NH$_4$)$_2$HPO$_4$ was formulated. About 2 ml concentrated HNO$_3$ was added dropwise thereto, and was dissolved by heating. The above Al$_2$O$_3$ support was impregnated with the aqueous solution, dried in a water bath at 60° C., and then further dried in the oven at 120° C. for 8 h, and calcined at 450° C. for 4 h. Thus, an oxidation state precursor of the catalyst was obtained.

Example 11

The catalyst in Example 11 was CoP/Al$_2$O$_3$ (Co/P=4, molar ratio). 10.0 g Al$_2$O$_3$ (20 to 40 mesh) was weighted. An 15 ml aqueous solution containing 4.93 g Co(NO$_3$)$_2$·6H$_2$O was formulated, dissolved by heating, and poured into the above Al$_2$O$_3$ support, and aqueous ammonia was added dropwise under stirring. The precipitate was deposited on the Al$_2$O$_3$ support which was then dried and calcined. Thereafter, 0.58 g (NH$_4$)$_2$HPO$_4$ was weighted and dissolved into 8 ml water by heating. The above Al$_2$O$_3$ support having CoO supported thereon was impregnated with the aqueous solution, dried in a water bath at 60° C., and then further dried in the oven at 120° C. for 8 h, and calcined at 450° C. for 4 h. Thus, an oxidation state precursor of the catalyst was obtained.

Before use, each of the oxidation state precursors of the catalysts in the above Examples 1 to 11 was reduced in situ in H$_2$=(GHSV=10000 h$^{-1}$) flow in a fixed bed reactor (diameter being 9 mm; height of the catalyst being 5 cm) under conditions of atmospheric pressure, and a temperature increasing from room temperature to 350° C. at 5° C./min and from 350° C. to 650° C. at 1° C./min, holding 3 h and then decreasing in H$_2$ flow to the reaction temperature, to obtain the catalyst. The conditions for CO hydrogenation reactions were as follows: the fixed bed reactor (diameter being 9 mm; height of the catalyst being 5 cm) at 280° C., 5.0 Mpa, H$_2$/CO (molar ratio being 2:1) mixed gas, and GHSV=5000$^{-1}$. After the effluent gas was passed through a cold trap and absorbed thoroughly by de-ionized water, the gaseous phase products were on-line analyzed, wherein the chromatograph was Agilent 3000 A Micro GC with four capillary columns of molecule sieve, Plot Q, Al$_2$O$_3$ and OV-1, and a TCD detector. The aqueous phase products were off-line analyzed with an FFAP capillary chromatogram column and a FID detector. Internal standard method was used for the analysis, and n-pentanol was used as internal standard substance.

The reaction results were summarized in Table 1.

Example 12

Before use, the oxidation state precursors of the catalyst in the Example 5 was reduced in situ in H$_2$ (GHSV=10000 h$^{-1}$) flow in a quartz fixed bed reactor (diameter being 4 mm; height of the catalyst being about 10 cm) under conditions of atmospheric pressure, and a temperature increasing from room temperature to 350° C. at 5° C./min and from 350° C. to 650° C. at 1° C./min, holding 3 h and then decreasing in H$_2$ flow to room temperature, and then transferred to a 1 liter volume of a slurry bed reactor under the protection of Ar flow and then the temperature of the reactor was raised to the reaction temperature in the H$_2$ flow (GHSV=10000 h$^{-1}$). The conditions for CO hydrogenation reactions were as follows: the slurry bed reactor (diameter being 8.2 mm; charge of the catalyst being 70 g, the content of the catalyst in the slurry being 10 (wt.)%), rotation speed=900 rpm) at 280° C., 5.0 Mpa, H$_2$/CO (molar ratio being 2:1) mixed gas, and GHSV=5000 h$^{-1}$. After the effluent gas was passed through a cold trap and absorbed thoroughly by de-ionized water, the gaseous phase products were on-line analyzed, wherein the chromatograph was Agilent 3000 A Micro GC with four capillary columns of molecule sieve, Plot Q, Al$_2$O$_3$ and OV-1, and a TCD detector. The aqueous phase products were off-line analyzed with an FFAP capillary chromatogram column and a FID detector. Internal standard method was used for the analysis, and n-pentanol was used as internal standard substance. At the same time, the slurry in the slurry bed reactor was sampled and analyzed. The analysis results were merged and then normalized to get the reaction result.

The reaction results were summarized in Table 1.

TABLE 1 the CO Hydrogenation Reaction Results of the Above Catalysts in the Examples

| | | Selectivity[a], % | | | | | |
|---|---|---|---|---|---|---|---|
| Example | CO Conversion % | Methane | Alkanes[b] | Methanol | Ethanol | oxygenate[c] | Carbon dioxide |
| 1 | 2.0 | 25.1 | 14.5 | 30.1 | 7.4 | 15.1 | 7.8 |
| 2 | 6.5 | 29.4 | 20.4 | 19.4 | 9.9 | 10.2 | 10.7 |
| 3 | 11.5 | 33.1 | 25.5 | 10.6 | 9.8 | 5.7 | 15.3 |
| 4 | 1.3 | 24.7 | 9.0 | 13.3 | 9.5 | 39.2 | 4.3 |
| 5 | 5.3 | 32.8 | 14.8 | 6.1 | 13.2 | 27.3 | 5.8 |

TABLE 1-continued the CO Hydrogenation Reaction Results of the Above Catalysts in the Examples

| Example | CO Conversion % | Selectivity[a], % | | | | | |
| --- | --- | --- | --- | --- | --- | --- | --- |
| | | Methane | Alkanes[b] | Methanol | Ethanol | oxygenate[c] | Carbon dioxide |
| 6 | 8.7 | 44.2 | 23.4 | 4.5 | 9.4 | 13.2 | 5.3 |
| 7 | 1.3 | 27.1 | 12.6 | 45.4 | 6.7 | 3.1 | 5.1 |
| 8 | 2.5 | 38.5 | 8.6 | 44.4 | 4.3 | 1.2 | 3.0 |
| 9 | 4.6 | 40.4 | 7.3 | 42.8 | 4.2 | 1.3 | 4.0 |
| 10 | 5.6 | 29.1 | 12.3 | 5.4 | 15.2 | 32.6 | 5.4 |
| 11 | 4.6 | 38.5 | 16.5 | 2.3 | 12.3 | 24.2 | 6.2 |
| 12 | 8.2 | 21.3 | 12.4 | 5.1 | 20.2 | 37.1 | 3.9 |

[a]Calculated based on the mole number of CO
[b]Alkanes except methane
[c]oxygenates with carbon number being no more than 5, except methanol and ethanol

What is claimed:

1. A supported catalyst for converting a syngas raw material into hydrocarbons and oxygenates, wherein
the supported catalyst comprises an active component and a support;
the active component is a mixture comprising a transition metal and a phosphide of the same transition metal, wherein the transition metal is one or more of Fe, Co, and Ni, wherein the weight percent of the active component in terms of metal is 0.5 to 30.0% by weight of the catalyst, wherein in the active component, the ratio of the mole number of the transition metal to the mole number of the phosphorous atoms is in the range of 1 to 10; and
the support is $SiO_2$ or $Al_2O_3$;
wherein the $SiO_2$ has a specific surface area of 100 to 600 $m^2/g$, and an average pore size of 5 to 90 nm; and the $Al_2O_3$ has a specific surface area of 100 to 400 $m^2/g$, and an average pore size of 4 to 90 nm.

2. The catalyst according to claim 1, wherein the weight percent of the active component in terms of metal is 1.0 to 25.0% by weight of the catalyst.

3. The catalyst according to claim 1, wherein the $SiO_2$ has a specific surface area of 200 to 400 $m^2/g$, and an average pore size of 10 to 50 nm.

4. The catalyst according to claim 1, wherein the $Al_2O_3$ has a specific surface area of 150 to 300 $m^2/g$, and an average pore size of 10 to 50 nm.

5. The catalyst according to claim 1, wherein the supported catalyst is consisted of the active component and the support.

6. A method for producing the catalyst according to claim 1, comprising supporting the active component on the support via an impregnation process or a precipitation process, and then calcining the resultant in air at 450° C.

7. The method according to claim 6, further comprising reducing the calcined catalyst in $H_2$ flow.

8. A method for producing hydrocarbons and oxygenates, comprising converting a syngas raw material into hydrocarbons and oxygenates, in the presence of a catalyst in a reactor, wherein:
the catalyst comprises an active component and a support;
the active component is a mixture comprising a transition metal and a phosphide of the same transition metal, wherein the transition metal is one or more of Fe, Co, and Ni, wherein the weight percent of the active component in terms of metal is 0.5 to 30.0% by weight of the catalyst, wherein in the active component, the ratio of the mole number of the transition metal to the mole number of the phosphorous atoms is in the range of 1 to 10; and
the support is $SiO_2$ or $Al_2O_3$;
wherein the $SiO_2$ has a specific surface area of 100 to 600 $m^2/g$, and an average pore size of 5 to 90 nm; and the $Al_2O_3$ has a specific surface area of 100 to 400 $m^2/g$, and an average pore size of 4 to 90 nm.

9. The method according to claim 8, wherein the reactor is a fixed bed or slurry bed reactor.

10. The method according to claim 8, wherein the method is performed under conditions of a temperature being 100 to 400° C., a reaction pressure being 1.0 to 10.0 MPa gauge, a $CO/H_2$ ratio by mole in the syngas being 0.5/1 to 10/1 and a space velocity being 100 to 10000 $h^{-1}$.

* * * * *